United States Patent [19]

Karrer et al.

[11] Patent Number: 4,749,654

[45] Date of Patent: Jun. 7, 1988

[54] METHOD AND APPARATUS FOR THE SUBMERGED GROWTH OF CELL CULTURES

[75] Inventors: Daniel Karrer, Uetikon a/See; Henry S. Bondi, Männedorf, both of Switzerland

[73] Assignee: Chemap AG, Männedorf, Switzerland

[21] Appl. No.: 321,893

[22] Filed: Nov. 16, 1981

[30] Foreign Application Priority Data

Nov. 18, 1980 [CH] Switzerland ............... 8542/80

[51] Int. Cl.$^4$ ............... C12N 5/02; C12M 3/02; B01D 29/14; B01D 13/00
[52] U.S. Cl. ............... 435/240.21; 435/240.25; 435/286; 435/818; 261/122; 210/150; 210/323.2; 210/321.6
[58] Field of Search ............... 435/240, 241, 284, 287, 435/286, 313, 315, 818, 314; 261/93, 122; 422/48; 210/433.2, 220, 321.1, 150, 323.2

[56] References Cited

U.S. PATENT DOCUMENTS

| | | | |
|---|---|---|---|
| 2,522,947 | 9/1950 | Hatch et al. | 435/314 |
| 3,647,632 | 3/1972 | Johnson et al. | 435/315 |
| 3,927,981 | 12/1975 | Viannay et al. | 435/284 |
| 3,997,396 | 12/1976 | Delente | 435/240 |
| 4,218,538 | 8/1980 | Church | 435/313 |
| 4,242,459 | 12/1980 | Chick et al. | 435/284 |
| 4,259,449 | 3/1981 | Katinger et al. | 435/241 |
| 4,308,351 | 12/1981 | Leighton et al. | 435/240 |
| 4,391,912 | 7/1983 | Yoshida et al. | 435/241 |
| 4,416,993 | 11/1983 | McKeown | 435/313 |
| 4,649,114 | 3/1987 | Miltenburger et al. | 435/240 |

FOREIGN PATENT DOCUMENTS

| | | | |
|---|---|---|---|
| 1448176 | 9/1976 | United Kingdom . | |
| 1530705 | 11/1978 | United Kingdom . | |
| 2059436 | 4/1981 | United Kingdom | 435/240 |
| 2075547 | 11/1981 | United Kingdom | 435/313 |

*Primary Examiner*—Elizabeth Weimar
*Attorney, Agent, or Firm*—Murray and Whisenhunt

[57] ABSTRACT

In a method and apparatus for the submersed growth of human and animal cell cultures, the cell growth container is provided with a centrally disposed permeator, which is formed simultaneously as conduit tube and reactor, and is provided on both sides with gas-permeable membranes. A gas of defined composition is led through the hollow porous support body of the permeator as fresh gas on one side, and led away on the other side as waste gas. In this manner the gas delivers oxygen across the membrane and receives carbon dioxide. The nutrient substrate and the tissue cells are held in suspension by means of a stirrer provided in the interior of the permeator. Foam problems do not occur, since no gas bubbles can enter into the medium.

11 Claims, 1 Drawing Sheet

4,749,654

METHOD AND APPARATUS FOR THE SUBMERGED GROWTH OF CELL CULTURES

BACKGROUND OF THE INVENTION

The invention concerns a method and an apparatus for the submerged growth of human and animal cell cultures per se, as well as cell cultures bound on microcarriers.

The growth of diploid cell cultures on solid supports is known. As supports for the cultures, so-called Roux flasks are used. With these flasks, only the air situated above the culture and the nutrient substrate serves for fumigation of the culture. Roller flasks constitute a further development, in which the nutrient medium is slowly moved so that gas exchange is expedited. It is also known to use rotating glass plates or glass tubes, which are immersed completely or partially in a culture medium. Herewith the effective surfaces, upon which the tissue cells can grow, are significantly greater.

Growth of cells on hollow fibers has also been described, for further increase of the effective surface. These comprise semi-permeable tube-like membranes.

A method and an apparatus is known from German patent publication DE-OS No. 2 319 120, with which tissue cells can colonize on the outer surface of a bundle of hollow filaments. The hollow filaments are composed of cellulose acetate and good gas-permeable silane-polycarbonate-copolymers. Nutrient material enriched with oxygen is led into the interior of the hollow filaments; the products of metabolism are discharged from the interior across the hollow filament membrane.

German patent publication DE-OS No. 24 31 450 also describes a method for the cultivation of cells using hollow filaments. Cells are bound aseptically to an outer or inner surface of atoxic hollow filament membranes. Air is led by pulsating flow through the interior of these hollow filament membranes.

A disadvantage is that a second layer of cells often forms in the generated layer of cells, which is cut off from gas exchange, the result being that its cells proceed to necrosis. The same occurs with cells still in suspension, which settle out.

The common disadvantage of all of these growth methods involving tissue cells fixed on a surface is that possible control of the physiological state of the culture is poor.

SUMMARY OF THE INVENTION

The object of the invention is to provide a submersed method for the growth of tissue cell cultures with indirect fumigation across gas-permeable membranes, as well as an apparatus for the accomplishment of the method, whereby a control of the physiological state of the cells is possible through measurement and regulation of characteristic features such as pH and $pO_2$, as well as $pCO_2$.

This object is achieved through a method for the submersed growth of tissue cell cultures by means of indirect fumigation across tube-like gas-permeable membranes of a permeator, which is thereby characterized in that the fresh gas supply and the waste gas removal ensue across the hollow support body of a permeator provided on both sides with gas-permeable membranes. The apparatus for accomplishment of the method is thereby characterized in that a tube-like permeator forms a vertical central tube in the container of the cell growth apparatus.

The support body of the permeator is composed of a porous tube, provided on both sides, i.e. inner and outer with a gas-permeable membrane of preferably Teflon or silicone polymer. Other gas-permeable membranes can also be used, provided that they exert no harmful influence on the cell growth. Under gas-permeable membranes are to be understood those which are suitable for gas diffusion.

A stirring rod provided inside of the permeator can transport not only from below to above but also the reverse. The stirrer may also be introduced into the permeator from above or below. Axially dispatched propeller stirrers, transverse-blade stirrers and vibration stirrers are suitable.

The fineness ratio, or degree of slimness, of a vessel is defined by the ratio of diameter to vessel height.

A fineness ratio from about 0.3 to 0.1, preferably 0.2 to 0.1, has proved to be suitable for the cell growth apparatus. The permeator insert should display a diameter from about 0.5 to 0.8, preferably 0.7, times the diameter of the container. The membrane thickness should amount to less than about 0.1 mm.

The cell growth container may be provided with measuring and operating mechanisms for control of $pO_2$, $pCO_2$, pH and temperature.

The novel features which are considered characteristic for the invention are set forth in particular in the appended claims. The invention itself, both as to its construction and procedure and its method of operation and use, together with additional objects and advantages thereof, will be best understood from the following description of specific embodiments when read in connection with the accompanying drawing.

DESCRIPTION OF THE PREFERRED EMBODIMENTS

Figure 1:
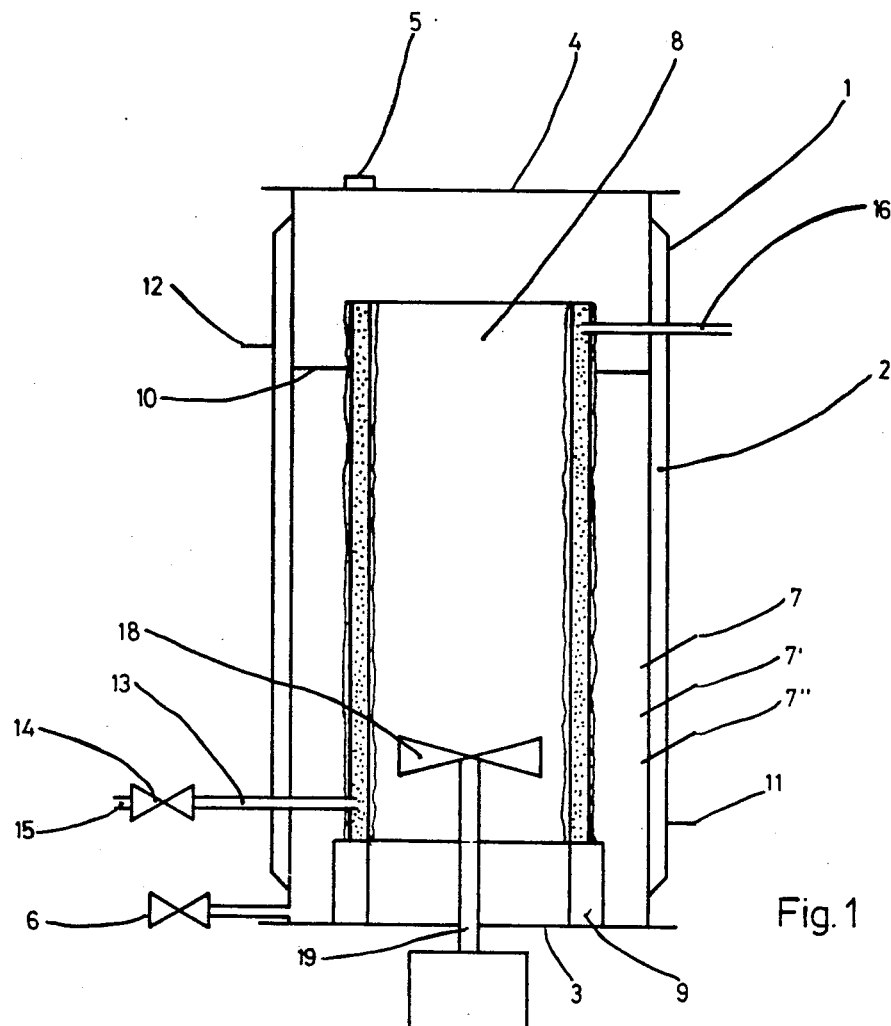
FIG. 1 is a schematic vertical section through the tissue cell growth apparatus according to the present invention.
Figure 2:
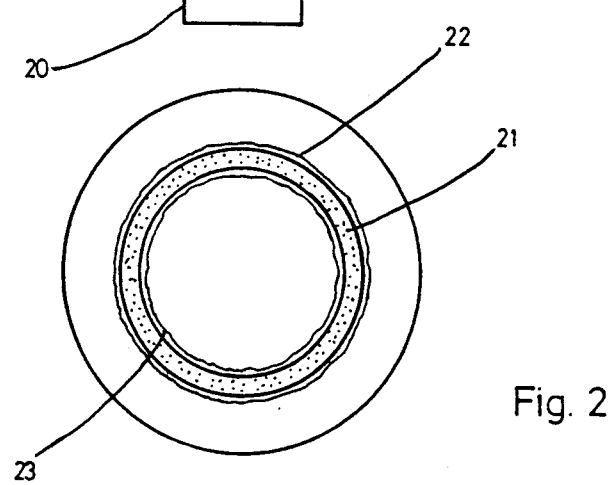
FIG. 2 is a cross-section through the permeator.

The cell growth apparatus is composed of a vertically distended glass or steel container 1, the ratio of diameter to height of which can amount to from about ⅓ to 1/10. The container 1 is provided with a double jacket 2, a base 3 and a cover 4. In the cover 4 are situated one or more sterile contacts 5. A harvesting valve 6 is installed in the bottom part of the container. The container wall is further provided with a connection 7 for oxygen and/or carbon dioxide measurement, a connection 7' for pH measurement, and a connection 7" for temperature measurement. A permeator 8 is placed in container 1 as central conduit tube, on glass or metal support 9, and is fastened at its upper end upon one or more reinforcements 10. The supports may also function as ring-shaped sealing means, closed gas-tight, with similar sealing means, i.e. a lid or cover, provided on the ring-shaped top surface of the permeator. The permeator 8 is composed mainly of a hollow, for example porous, support body 21, an outer gas-permeable membrane 22, and an inner gas-permeable membrane 23. The double jacket is provided with an input connection 11 and an output connection 12 for the heat-exchange medium. The permeator 8 is linked across a conduit piece 13 and a valve 14 with a gas-collecting main 15. The gas conduit 15 is fed by a gas-dosing device, which is not shown in the drawing. A waste gas conduit 16 leads to the open air. A stirrer 18 is fixed to the lower part of the permeator and connected across a drive shaft 19 with an electric motor 20.

In operation, container 1 of the tissue cell growth apparatus is filled with previously sterilized nutrient substrate and tissue cells, in particular with diploid human cells. The stirrer 18 keeps the cells in suspension. Simultaneously, gas, composed of at most 5% by volume $CO_2$, up to 20% by volume $O_2$, and up to 50% by volume $N_2$, the remainder displaying the composition of air, flows from a not shown mixing block into the gas-collecting main 15, the valve 14 and the conduit 13 and to the hollow space of the porous support body 21. The oxygen in the nutrient solution is able to diffuse not only through the outer membrane 22 but also through the inner membrane 23, and simultaneously $CO_2$ from the nutrient solution diffuses back into the interior of the hollow support body. The gas, enriched in this manner with $CO_2$, leaves the interior between both membranes across conduit 16.

The result is a gas exchange without the occurrence of air bubbles entering into the nutrient substrate and coming as such into contact with the tissue cells. In this manner any foam formation is also avoided.

The carrier for oxygen and carbon dioxide can be gaseous or liquid. Air or other gas enriched with oxygen comes into consideration as gaseous carrier. As liquid carrier, fluorinated hydrocarbons or complete nutrient medium, for example, may be used.

The method according to the present invention may, in addition to entirely submersed growth, be performed using microcarriers in similar manner.

The apparatus according to the present invention displays numerous advantages:
large material exchange surface
defined flow pattern in the reactor
good homogeneity of the suspension
small shearing stress through use of a slowly running axial stirrer (sedimentation of the carrier must be prevented)
very simple and easy to calculate scaling-up
no foam problem, therefore no cell concentration in foam
little serum concentration, since little shearing stress
control of $pCO_2$ and $pO_2$ is possible
use of pure oxygen for fumigation is possible
small medium consumption as a result of combination of permeator and reactor
with high $O_2$-requirements, concentric central tube makes possible an increase in surface area
simple cleaning
better utilization of fermentor volume
in situ sterilizability.

It will be understood that each of the elements described above, or two or more together, may also find a useful application in other types of cell cultivations differing from the types described above.

While the invention has been illustrated and described as embodied in a method and apparatus for the submersed growth of cell cultures, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. Method for the submersed growth of tissue culture cells in a cell growth apparatus comprising a container, a stirrer located in the container, and an annular porous support body having interior and exterior sides and an interior and having cleanable gas-permeable membranes of a thickness no greater than about 0.1 mm on the interior and exterior sides of the support body, said support body located within the container,
   said method comprising
   introducing tissue culture cells and nutrient solution into the container,
   introducing oxygen into the interior of the support body,
   and cultivating the tissue culture cells by stirring the container contents to circulate the tissue culture cells and nutrient solution in the container while diffusing oxygen from the support body interior across the membranes to the nutrient solution and diffusing $CO_2$ from the nutrient solution across the membranes to the support body interior.

2. Method according to claim 1, wherein the fresh gas supply and waste gas removal are carried out by means of liquid as carrier for $O_2$ and $CO_2$.

3. Method according to claim 2, wherein nutrient medium alone is used as carrier liquid.

4. Method of claim 1, wherein the container is heated by means of an external jacket containing heat-exchange medium.

5. Cell growth apparatus comprising
   container means for containing tissue culture cells and nutrient solution;
   stirring means for circulating the tissue culture cells and the nutrient solution within the container;
   permeator means located within the container means for diffusing oxygen into the nutrient solution and for removing $CO_2$ from the nutrient solution, said permeator means including an annular porous support body having interior and exterior sides and an interior and having cleanable gas-permeable membranes of a thickness no greater than about 0.1 mm on the interior and exterior sides of the support body;
   supply means for introducing oxygen into the interior of the support body; and
   removal means for removing carbon dioxide from the interior of the support body.

6. Apparatus according to claim 5, wherein support body is a porous cylinder.

7. Apparatus according to claim 5, wherein the support body is a perforated tube.

8. Apparatus according to claim 5, wherein the container means has a fineness ration of about 0.3 to 0.1.

9. Apparatus according to claim 5, wherein the permeator means has a diameter of from about 0.5 to 0.8 times the container means diameter.

10. Apparatus according to claim 5, further comprising ring-shaped sealing means closed gas-tight at a top and a bottom of the permeator.

11. Apparatus according to claim 5 additionally including a heat exchange jacket surrounding the container means.

* * * * *